United States Patent

Raal

[11] Patent Number: 5,996,854
[45] Date of Patent: Dec. 7, 1999

[54] LIQUID DISPENSER WITH COAXIAL PISTON AND ROD FOR DISPENSING A PRECISE VOLUME

[76] Inventor: Johan David Raal, c/o University of Natal, Chemical Engineering, Private Bag X10, Dalbridge, 4014 Kwa Zulu Natal, South Africa

[21] Appl. No.: 09/041,747

[22] Filed: Mar. 13, 1998

[51] Int. Cl.$^6$ .................................................. G01F 11/00
[52] U.S. Cl. ........................ 222/309; 222/333; 222/386
[58] Field of Search ................................ 222/309, 333, 222/386

[56] References Cited

U.S. PATENT DOCUMENTS

| | | | |
|---|---|---|---|
| 4,101,283 | 7/1978 | Sundstrom | 222/333 |
| 4,228,924 | 10/1980 | Gilbert | 222/309 |
| 5,022,556 | 6/1991 | Dency et al. | 222/309 |
| 5,035,270 | 7/1991 | Herzog | 222/309 |
| 5,067,531 | 11/1991 | Herzog | 222/309 |
| 5,348,585 | 9/1994 | Weston | 222/333 |
| 5,467,899 | 11/1995 | Miller | 222/309 |

*Primary Examiner*—Joseph A. Kaufman
*Attorney, Agent, or Firm*—Young & Thompson

[57] ABSTRACT

A liquid dispensing device for use in the dispensing of micro-volumes of liquid for gas chromatography has a cylinder with an open end and has a piston slidable therein. The piston has a coaxial rod slidable within itself; and displacement member including a reversible stepper motor and clutch mechanism is provided to effect selectable linear displacement of the piston in the cylinder and/or the rod in the piston in order to vary to volume of the cylinder, the top end of which is in communication with the fluid sample to be injected.

16 Claims, 2 Drawing Sheets

LIQUID DISPENSER WITH COAXIAL PISTON AND ROD FOR DISPENSING A PRECISE VOLUME

FIELD OF THE INVENTION

This invention relates to a liquid dispensing device and in particular a device for dispensing controlled micro-volumes of liquid. The device finds particular application in the field of gas chromatography.

BACKGROUND OF THE INVENTION

Gas chromatography requires the preparation of controlled gas-vapor mixtures for the purpose of calibration and analysis. This procedure involves the introduction of a precise volume of liquid into a chamber containing a carrier gas of known properties, the liquid being instantly vaporized to form a gas-vapor mixture. Typically this procedure is carried out by manual injection using micro-syringes. There are obvious disadvantages to this procedure in that it requires a practiced hand to fill the syringe with a bubble-free sample and then inject repetitively so that consistent results are achieved. Both the calibration standard and the sample must be injected several times to ensure accurate results.

In a syringe there must be perfect sealing between the plunger or piston and the barrel along its entire length. This becomes a problem, particularly, in micro-syringes where the plunger is a very thin rod that can bend or deform easily after short usage.

The same criteria for standard and sample delivery into the chamber apply to high performance liquid chromatography. In some ways the procedure is more arduous in that samples must be degassed, and more care is required because of large sample volumes and larger syringes.

It is therefor an object of this invention to provide a liquid dispensing device which overcomes or at least minimizes these problems and provides repeatable delivery of a gas free sample.

THE INVENTION

According to the invention, a liquid dispensing device comprises a cylinder having an open end and including a piston slidable therein, the piston including a coaxial rod slidable within the piston; and displacement means adapted to effect selective linear displacement of the piston in the cylinder and/or the rod within the piston in order to vary the volume of the cylinder.

In the preferred form of the invention, the rod protrudes a predetermined distance into the cylinder body and the point of exit of the protrusion from the piston is sealed, preferably by means of an O-ring. Unlike in a syringe, this sealing is at a single point and a mechanism is used to tighten the O-ring around the rod at the seal.

Also in the preferred form of the invention, the upper end of the interior of the cylinder is dome shaped.

The displacement means may include a reversible stepper motor and a clutch mechanism is preferably provided to facilitate vertical movement of the piston and rod together when it is engaged. Disengagement of the clutch permits movement of the rod only.

In a typical chromatographical situation the top end of the cylinder is in communication with the liquid sample to be injected by means of a micro-capillary, via a rotary valve. In operation, the clutch is engaged and the piston is moved down the cylinder to draw sample into the cylinder body. The valve is then rotated and upward movement of the piston expels the uppermost portion of the liquid together with any air bubbles to waste. This step may be repeated once or twice. The domed shape of the cylinder ensures that no air bubbles remain in the cylinder, valve or in the capillary tube. The device is now set for discharge of the sample into the chromatograph chamber. The valve is reorientated and the clutch is disengaged. The stepper motor advances the rod upwards through the stationary piston to displace a volume of liquid from the filled cylinder, through the valve. The volume discharged is proportional to the volume of the portion of the rod inserted into the fixed pool of liquid contained in the cylinder.

The precise volume discharged can be calculated using the rod movement. This is obtained by counting the stepper motor steps or alternatively, by means of a micrometer attached to the motor shaft, and from the pitch of the threads on the drive shaft and the exact diameter of the rod which are known.

In the preferred form of the invention the displacement means includes a nut coaxial with the piston and rod, the nut being rotatable on an externally threaded portion of the piston and being in disengageable communication with a stepper motor adapted to effect linear displacement of the piston. The displacement means may further include a second nut coaxial with the piston and rod, the rod including a plate member at the base thereof for attachment to the nut and, the nut being in further permanent rotatable communication with the stepper motor by means of a threaded shaft. This second nut is adapted to facilitate linear displacement of the rod within the piston.

Whereas the second nut is in permanent communication with the stepper motor, a clutch mechanism is provided to engage or disengage the first nut from the motor. This arrangement ensures that the motor will always cause rotation of the threaded motor shaft. If the clutch is engaged the first nut will be rotated causing simultaneous sliding of the piston and rod. If the clutch is disengaged, the rod will slide within the piston which will remain stationary.

In the preferred form of the invention the clutch is electromechanical with one or more solenoid coils being provided having retractable locking pins adapted to engage complemental slots when the solenoid is energized to engage the clutch. An alternative clutch arrangement involves a single fixed solenoid coil which can attract or repel magnetized locking pins.

The volumes required to be discharged for gas chromatographic purposes are minute and it is desired that the injection samples having volumes of the order of pico liters may be dischargeable by the device of the invention.

In one form, a stepper motor capable of rotation in two hundred steps per revolution is provided and this together with a thread pitch of 1 mm on the piston and 0.5 mm on the rod results in linear advancement of the piston by 0.005 mm and the rod 0.0025 mm per motor step. Alternatively, the two threaded pitches may be the same.

The device may be provided with a housing which is adapted to support the displacement means relative to the motor.

EMBODIMENT OF THE INVENTION

An embodiment of the invention is described below with reference to the accompanying drawings in which.

Figure 1:
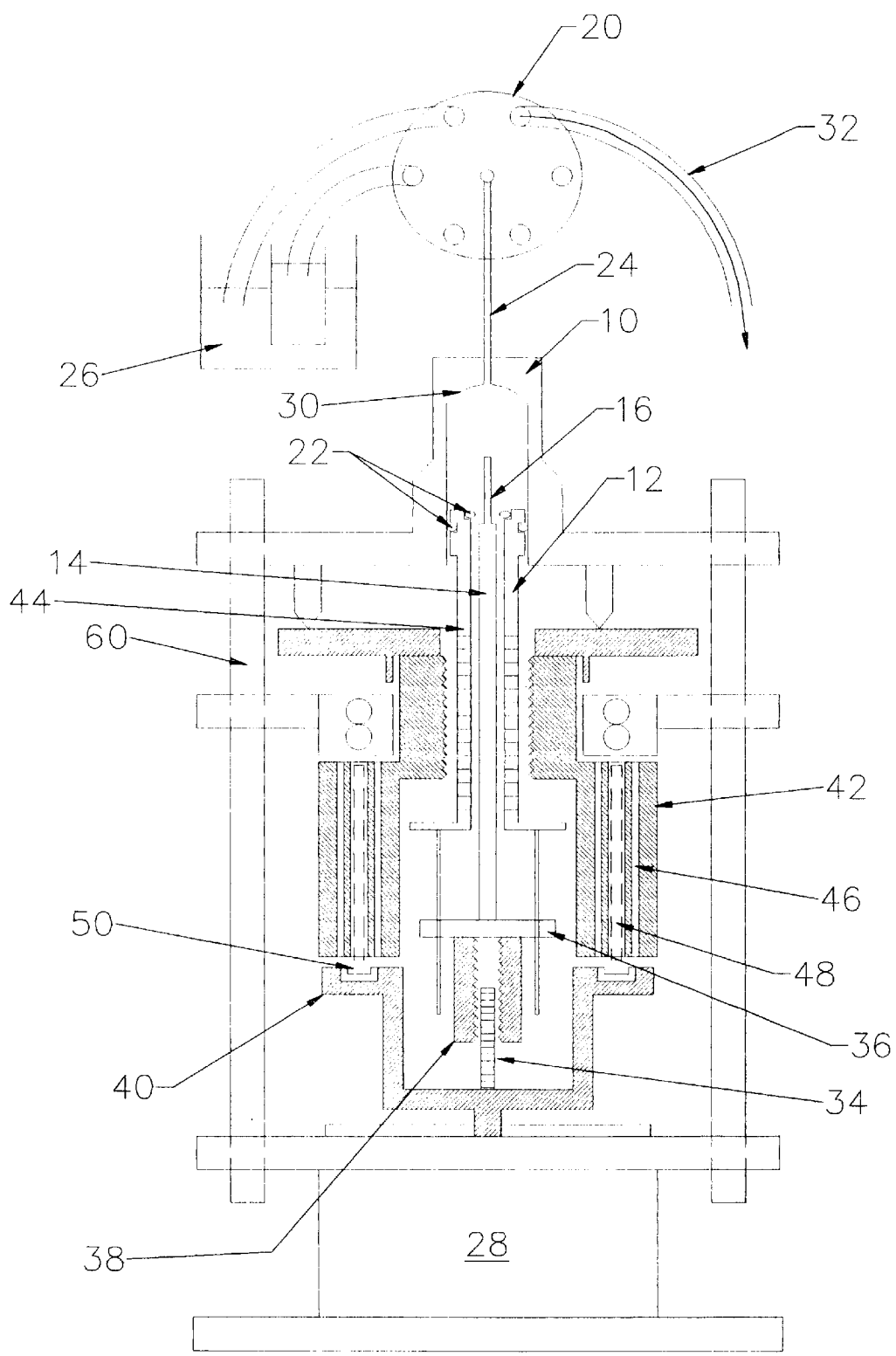
FIG. 1 is a sectional view through a device according to the invention.
Figure 2:
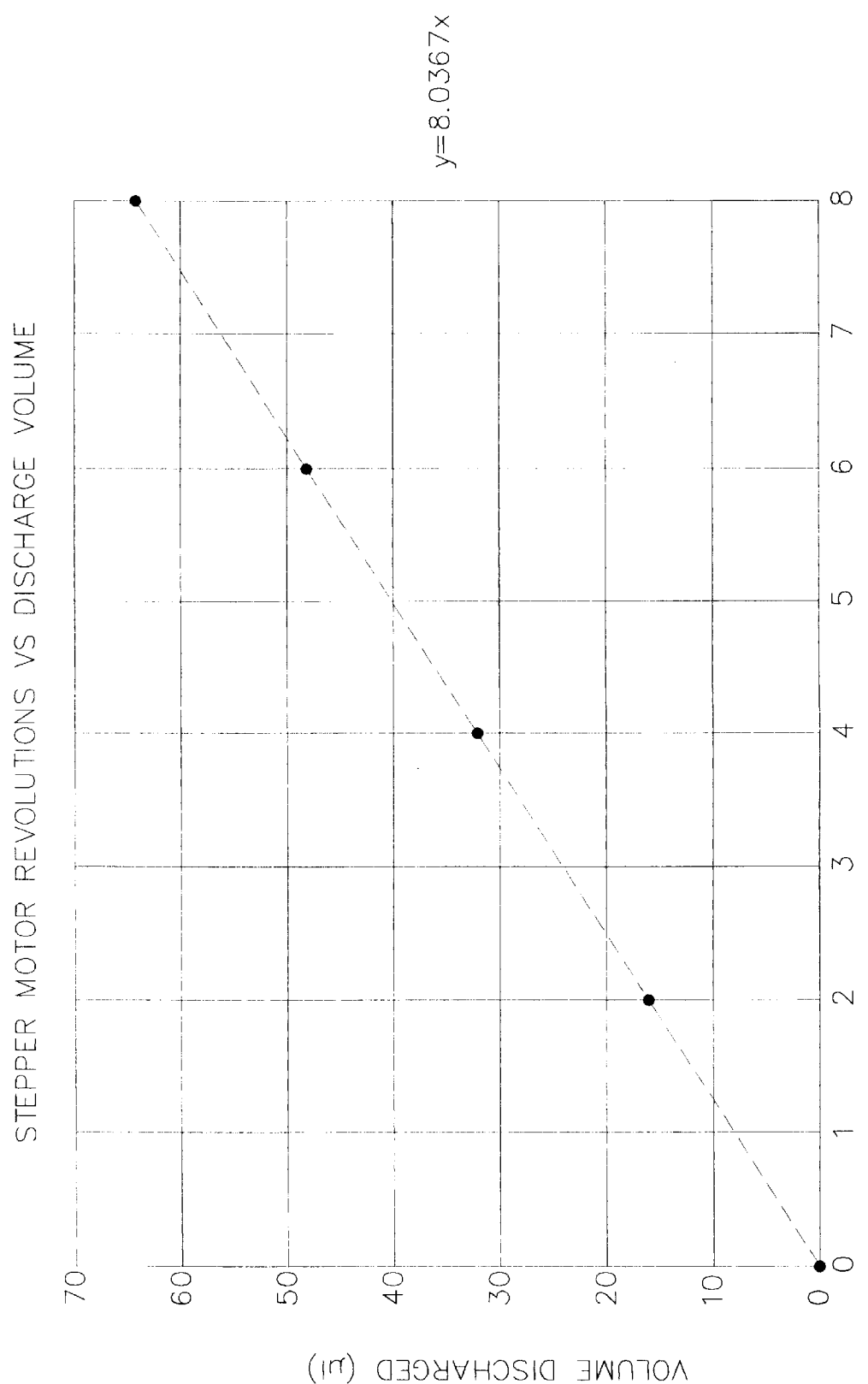
FIG. 2 is a graph relating to the very accurate data obtained with the device, in which the measured volume of liquid discharged is exactly proportional to the stepper motor revolutions.

In the drawing, a liquid dispensing device comprises a cylinder 10 having a piston 12 slidable therein. The piston has a coaxial rod 14 slidable within the piston 12. The rod has a protrusion 16 and may be advanced into the body 18 of the cylinder either on its own, or in conjunction with the piston to effect discharge of liquid from 18 into a gas chromatograph for analysis via rotary port valve 20. O-rings 22 are provided to seal the cylinder.

In operation, the valve 20 is rotated to permit liquid sample to be drawn through the valve into the body of the cylinder 18 via micro capillaries in 24. This is effected by engaging the clutch mechanism and moving the piston and rod together downwards. The valve is then reorientated to expel to the waste container 26, and the direction of the stepper motor 28 is reversed. With the clutch still engaged the piston and rod move upwards together to expel the uppermost portion of the liquid to waste along with any air bubbles which may be present. The domed roof 30 of the cylinder prevents bubbles from collecting and remaining in the cylinder, valve or micro-capillary.

The rotary valve is then re-orientated and set for discharge or injection into the gas chromatograph or other desired volume. The clutch is disengaged so that the stepper motor causes advancement of the rod only along the piston shaft to displace a predetermined volume of liquid from the cylinder body 18, into the gas chromatograph via micro-capillary 32.

The stepper motor 28 effects movement of the piston and rod by rotating threaded shaft 34. The bottom end of the rod 14 includes a plate 36 to which is fixed a nut 38 (the second coaxial nut described above). This nut rotates on the threaded shaft 34 and results in upward or downward sliding of the rod.

The threaded shaft includes a formation 40 adapted to engage a further nut 42 (the first coaxial nut) which is rotatable on an externally threaded portion 44 of the piston. An electromagnetic clutch facilitates engagement of this formation and when the clutch is engaged, the stepper motor effects movement of the piston and rod in tandem. When disengaged, only the rod moves as described above.

The clutch is of an electromagnetic nature and comprises one or more solenoid coils 46 with the walls of the nut 42 and retractable locking pins 48. Energizing the coil causes the pin to engage or disengage the slots 50 cut in formation 40.

Housing 60 supports the piston and rod in position relative to the stepper motor.

I claim:

1. A liquid dispensing device comprises a cylinder having an open end and including a piston slidable therein, the piston including a coaxial rod slidable within the piston 3; and displacement means adapted to effect selective linear displacement of the piston in the cylinder and the rod within the piston in order to vary the volume of the cylinder.

2. The liquid dispensing device according to claim 1 in which the rod protrudes a predetermined distance into the cylinder and a point of exit of the protrusion from the piston is sealed.

3. The liquid dispensing device according to claim 2 in which the sealing is effected by an O-ring.

4. The liquid dispensing device according to claim 1 in which the upper end of the interior of the cylinder is dome shaped.

5. The liquid dispensing device according to claim 1 in which the displacement means includes a reversible stepper motor and a clutch mechanism is provided to facilitate vertical movement of the piston and rod together when it is engaged.

6. The liquid dispensing device according to claim 5 in which disengagement of the clutch permits movement of the rod only.

7. The liquid dispensing device according to claim 1, in which the top end of the cylinder is in communication with a liquid sample to be injected by means of a micro-capillary tube, via a rotary valve.

8. The liquid dispensing device according to claim 1 in which the displacement means includes a nut coaxial with the piston and rod, the nut being rotatable on an externally threaded portion of the piston and being in disengageable communication with a stepper motor adapted to effect linear displacement of the piston.

9. The liquid dispensing device according to claim 8 including a second nut coaxial with the piston and rod, the rod including a plate member at the base thereof for attachment to the nut and the nut being in further permanent rotatable communication with the stepper motor by means of a threaded shaft.

10. The liquid dispensing device according to claim 9 in which a clutch mechanism is provided to engage or disengage the first nut from the motor.

11. The liquid dispensing device according to claim 10 in which the clutch is electromechanical with one or more solenoid coils being provided having retractable locking pins adapted to engage complemental slots when the solenoid is energized to engage the clutch.

12. A liquid dispensing device comprising:
   a cylinder having an open end and including a piston slidable therein, said piston including a coaxial rod slidable within the piston; and
   displacement means adapted to effect selective linear displacement of one of said piston in said cylinder and said rod within said piston, in order to vary a volume of said cylinder.

13. A liquid dispenser comprising:
   a cylinder having an open end through which liquid is dispensed;
   a piston slidable within said cylinder;
   a rod that is coaxial with and slidable within said piston;
   a first nut engaging said piston that selectively displaces said piston and said rod together within said cylinder when said first nut is rotated; and
   a second nut connected to said rod that selectively displaces only said rod within said cylinder when said second nut is rotated.

14. The dispenser of claim 13, further comprising a motor and a clutch that selectively connects said first nut to said motor.

15. The dispenser of claim 14, further comprising a screw connected to said motor that engages said second nut.

16. The dispenser of claim 13, wherein said first nut engages threads on an exterior of said piston.

* * * * *